United States Patent
Champie

(10) Patent No.: US 11,253,443 B2
(45) Date of Patent: Feb. 22, 2022

(54) SKIN PRODUCTS WITH C60 AND NIACIN

(71) Applicant: Max C. Champie, Buena Vista, CO (US)

(72) Inventor: Max C. Champie, Buena Vista, CO (US)

(*) Notice: Subject to any disclaimer, the term of this patent is extended or adjusted under 35 U.S.C. 154(b) by 0 days.

(21) Appl. No.: 16/790,603

(22) Filed: Feb. 13, 2020

(65) Prior Publication Data

US 2021/0220237 A1 Jul. 22, 2021

Related U.S. Application Data

(63) Continuation-in-part of application No. 16/749,916, filed on Jan. 22, 2020, now Pat. No. 10,842,738.

(51) Int. Cl.
| | | |
|---|---|---|
| *A61K 8/19* | (2006.01) | |
| *A61K 8/9794* | (2017.01) | |
| *A61Q 19/08* | (2006.01) | |
| *A61K 8/49* | (2006.01) | |
| *A61K 8/36* | (2006.01) | |

(52) U.S. Cl.
CPC ............... *A61K 8/19* (2013.01); *A61K 8/361* (2013.01); *A61K 8/4926* (2013.01); *A61K 8/9794* (2017.08); *A61Q 19/08* (2013.01)

(58) Field of Classification Search
CPC ........ A61K 8/19; A61K 8/9794; A61K 8/361; A61K 8/4926; A61Q 19/08
See application file for complete search history.

(56) References Cited

U.S. PATENT DOCUMENTS

| | | | | |
|---|---|---|---|---|
| 2004/0009200 A1* | 1/2004 | Seyler | ...................... | A61K 8/35 424/401 |
| 2006/0134095 A1* | 6/2006 | Ito | ........................... | A61P 39/06 424/125 |
| 2008/0057088 A1* | 3/2008 | Blass | ................... | A61K 8/9794 424/401 |
| 2009/0246234 A1 | 10/2009 | Johnson | | |
| 2011/0293588 A1* | 12/2011 | McCleary | ............ | A61K 31/122 424/94.1 |
| 2019/0008825 A1 | 1/2019 | Murphy | | |
| 2019/0231670 A1* | 8/2019 | Pujos | ...................... | A61K 8/671 |
| 2019/0350851 A1* | 11/2019 | Tasset | ................ | A61K 47/6949 |
| 2020/0054061 A1* | 2/2020 | Dischler | .................. | A23L 33/12 |

FOREIGN PATENT DOCUMENTS

| CN | 106236674 A | * | 12/2016 |
|---|---|---|---|
| CN | 108125803 A | * | 6/2018 |
| CN | 108852865 | | 11/2018 |
| CN | 108969435 | | 12/2018 |
| CN | 109498478 | | 3/2019 |
| CN | 109820739 | | 5/2019 |
| CN | 109820739 A | * | 5/2019 |

OTHER PUBLICATIONS

"Paul's Choice Skin Care," Food and Chemical Toxicology, Jan. 2000, Issue 1, p. 79-98.*
Thompson, Donna A.; et al. "Tetrahydracurcumin-reated Allergic Contact Dermatitis," Contact Dermatitis, Department of dermatology, University Hospital of North Staffordshire NSH Trust, 2006. pp. 254-255.
National Institute of Health. "Niacin Fact Sheet for Health Professionals". pp. 1-19.
"Caprylic/Capric Triglyceride," Food and Chemical Technology, Jan. 2000, issue 1. pp. 79-98.

* cited by examiner

*Primary Examiner* — Jared Barsky
(74) *Attorney, Agent, or Firm* — Fish IP Law, LLP

(57) ABSTRACT

A skin product having primary ingredients fullerene, niacin, and at least one of curcumin and tetrahydracurcumin. In some embodiments, the skin product additionally contains a medium-chain fatty acid, as a primary ingredient. Preferably, fullerene is C60, and the medium-chain fatty acid is C8 caprylic acid. The skin product is preferably made by mixing niacin and curcumin (or tetrahydracurcumin) first, then adding the medium-chain fatty acid, and finally mixed with fullerene. The skin product can be used to treat skin conditions (e.g., burn, wrinkles).

12 Claims, No Drawings

SKIN PRODUCTS WITH C60 AND NIACIN

CROSS-REFERENCE TO RELATED APPLICATIONS

This application claims priority to, and is a continuation in part (CIP) of, U.S. Utility application Ser. No. 16/749,916, titled "Skin product using C60 and Curcumin" by the same inventor, filed on Jan. 22, 2019, which is incorporated herein by reference in its entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is skin products.

BACKGROUND

The following description includes information that may be useful in understanding the present invention. It is not an admission that any of the information provided herein is prior art or relevant to the presently claimed invention, or that any publication specifically or implicitly referenced is prior art.

Fullerenes are considered as free radical scavengers capable of eliminating reactive oxygen species (ROS). Chinese patent applications CN108852865A and CN109498478A to Hui Li et al, teaches using fullerene for cosmetic purposes. Additionally, many ingredients can be used in skin products for healing and anti-aging purposes. For example, United States Patent Application Publication No. US 2019/0008825 A1 by Murphy, et al, teaches using hundreds of compounds to treat skin conditions due to reactive oxygen species production in the skin. United States Patent Application Publication No. US 2009/0246234 to Johnson teaches using niacin and niacinamide in topical skin compositions to treat certain skin disorders. However, niacin has side effects (redness, or tingly skin) that discourages its use on the skin. Prior work has yet to combine fullerene with selective ingredients to produce enhanced anti-aging properties and reduced side effects.

Thus, there is still a need for skin products having enhanced anti-aging properties and reduced side effects.

DETAILED DESCRIPTION OF THE INVENTION

The inventive subject matter provides composition and methods in which skin products containing, as primary ingredients, fullerene, curcumin (and/or tetrahydracurcumin), niacin, and a medium-chain fatty acid, having enhanced healing and anti-aging properties and minimal side effects.

A fullerene is an allotrope of carbon whose molecule consists of carbon atoms connected by single and double bonds so as to form a closed or partially closed mesh, with fused rings of five to seven atoms. Buckminsterfullerene is a fullerene with the formula C60. In especially preferred embodiments, buckminsterfullerene C60 is used as the fullerene.

Niacin, also known as nicotinic acid, is an organic compound with the formula $C_6H_5NO_2$ and a form of vitamin B3, an essential human nutrient. Medium-chain fatty acids (MCFAs) are saturated or unsaturated fatty acids found at high concentrations in food such as coconut oil. Contemplated medium-chain fatty acids include caproic acid (C6), caprylic acid (C8), capric acid (C10), and lauric acid (C12).

A curcuminoid is a linear diarylheptanoid, with molecules such as curcumin or derivatives of curcumin with different chemical groups that have been formed to increase solubility of curcumins and make them suitable for drug formulation. These compounds are natural phenols and produce a pronounced yellow color. Curcumin is the major polyphenol in the spice turmeric. Tetrahydracurcumin is a colorless hydrogenated derivative of the natural yellow curcuminoids. Tetrahydrocurcumin has differing positive effects and color from curcumin. Either curcumin or tetrahydrocurcumin could be utilized depending on the health issue being treated. It is further contemplated that curcumin and tetrahydrocurcumin are used in combination.

In preferred embodiments, niacin and curcumin (and/or tetrahydracurcumin) are mixed first, then mixed with the medium-chain fatty acid, and then mixed with fullerene (e.g., C60). This sequential addition ensures that niacin, curcumin and medium-chain fatty acid bond first and then are absorbed inside the C60 structure, resulting a homogeneous mixture of niacin, curcumin and medium-chain fatty inside C60.

When used alone, niacin produced the side effect of "niacin flush", which appears as a flush of red on the skin, accompanied by an itching or burning sensation. Moreover, an increasing number of patients could be developing contact allergic dermatitis to this allergen, as multiple cases of contact allergy to tetrahydracurcumin has been described. See Thompson D A, Tan B B, Tetrahydracurcumin-related allergic contact dermatitis. Contact Dermatitis. 2006 October; 55(4):254-5.

However, as observed in human volunteers, when C60, niacin, curcumin and C8 caprylic acid are used together, surprisingly side effects that might be expected when some of these ingredients are used alone are reduced. The side effect of niacin is minimized, as human volunteers only feel transient niacin flush, and the redness and burning sensation quickly subside within 10-15 min, and no allergic reaction to curcumin or tetrahydrocurcumin was observed in human volunteers.

In preferred embodiments, the skin product is packaged as a facial spray used for burn victims. It is contemplated that the facial spray should be used two to three times a day. Preferably, face is washed before applying liberally to the face. The user can rub it in or just let dry. It is contemplated using before bed would lead to optimal results.

The inventive subject matter also provides methods for treating skin conditions. Contemplated skin conditions that can be treated or prevented with the composition and methods described herein include eczema (atopic dermatitis), acne, sunburn, skin wrinkles, skin lines, age spots, hyperpigmentation and other signs of skin aging.

The inventive subject matter also teaches methods of making a skin product. First step: mixing niacin and curcumin (or tetrahydrocurcumin) to form a first mixture; second step: adding a medium-chain fatty acid to the first mixture to form a second mixture; last step: adding a fullerene to the second mixture to form a third mixture. This is the ensure that niacin, medium-chain fatty acid, and curcumin (or tetrahydrocurcumin) are mixed evenly inside fullerene molecules.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A skin product, comprising a plurality of fullerenes each comprising a plurality of carbons covalently bonded to one another and each circumscribing an enclosed internal volume, niacin, a medium chain triglyceride, and at least one of curcumin and tetrahydrocurcumin, wherein niacin, the medium chain triglyceride and at least one of curcumin and tetrahydrocurcumin are disposed within the enclosed internal volumes of the plurality of fullerenes, wherein the skin product is formulated for topical application, and wherein niacin and at least one of curcumin and tetrahydrocurcumin are combined to form a first mixture, wherein the first mixture is contacted with the medium chain fatty acid to form a second mixture, and wherein the second mixture is contacted with the fullerenes, such that niacin, the medium chain fatty acid, and at least one of curcumin and tetrahydrocurcumin are homogeneously distributed within the enclosed internal volumes of the fullerenes and wherein niacin flushing does not occur upon topical application.

2. The skin product of claim 1, wherein the fullerene is C60.

3. The skin product of claim 2, comprising curcumin, but not tetrahydrocurcumin.

4. The skin product of claim 2, comprising tetrahydrocurcumin, but not curcumin.

5. The skin product of claim 1, wherein the medium-chain fatty acid comprises C8 caprylic acid.

6. A skin product, wherein active ingredients consist essentially of a plurality of fullerenes comprising a plurality of carbons covalently bonded to one another and each circumscribing an enclosed internal volume, niacin, a medium chain triglyceride, and at least one of curcumin and tetrahydrocurcumin, wherein niacin is disposed within the enclosed internal volumes of the plurality of fullerenes, wherein the skin product is formulated for topical application, and wherein niacin and at least one of curcumin and tetrahydrocurcumin are combined to form a first mixture, wherein the first mixture is contacted with the medium chain fatty acid to form a second mixture, and wherein the second mixture is contacted with the fullerenes, such that niacin, the medium chain fatty acid, and at least one of curcumin and tetrahydrocurcumin are homogeneously distributed within the enclosed internal volumes of the fullerenes and wherein niacin flushing does not occur upon topical application.

7. The skin product of claim 6, wherein the active ingredients consist essentially of curcumin, but not tetrahydrocurcumin.

8. The skin product of claim 7, wherein the fullerene is C60.

9. The skin product of claim 7, wherein the medium-chain fatty acid is C8 caprylic acid.

10. The skin product of claim 6, wherein the active ingredients consist essentially of tetrahydrocurcumin, but not curcumin.

11. The skin product of claim 10, wherein the medium-chain fatty acid is C8 caprylic acid.

12. The skin product of claim 1, wherein the skin product is formulated as facial spray.

* * * * *